US007229028B2

(12) United States Patent

Chen et al.

(10) Patent No.: US 7,229,028 B2
(45) Date of Patent: Jun. 12, 2007

(54) AEROSOL IMPINGEMENT BAFFLE

(75) Inventors: Wen-Pin Chen, Taipei (TW); Kevin Cheng, Taipei (TW); Chih-Hung Huang, Taipei (TW)

(73) Assignee: Kai Chih Industrial Co., Ltd., Taipei (TW)

( * ) Notice: Subject to any disclaimer, the term of this patent is extended or adjusted under 35 U.S.C. 154(b) by 0 days.

(21) Appl. No.: 10/339,329

(22) Filed: Jan. 10, 2003

(65) Prior Publication Data

US 2004/0050952 A1 Mar. 18, 2004

(30) Foreign Application Priority Data

Sep. 18, 2002 (TW) ............................. 91214744 U

(51) Int. Cl.
*B05B 17/06* (2006.01)
*B05B 1/08* (2006.01)
*B05B 1/26* (2006.01)
*B05B 1/14* (2006.01)
*A61M 11/00* (2006.01)

(52) U.S. Cl. ............................... 239/102.2; 239/102.1; 239/556; 239/568; 239/370; 239/601; 128/200.16

(58) Field of Classification Search ............. 239/102.1, 239/102.2, 556, 568, 370, 338, 498–501, 239/504, 518, 522, 524, 548, 557, 601; 128/200.16, 128/200.14, 200.18; 251/127
See application file for complete search history.

(56) References Cited

U.S. PATENT DOCUMENTS

| | | | | |
|---|---|---|---|---|
| 3,061,204 | A * | 10/1962 | Macinnes et al. | 239/500 |
| 4,746,067 | A * | 5/1988 | Svoboda | 239/338 |
| 4,976,259 | A * | 12/1990 | Higson et al. | 128/200.18 |
| 5,261,601 | A * | 11/1993 | Ross et al. | 239/102.2 |
| 5,533,501 | A * | 7/1996 | Denyer | 128/200.21 |
| 5,685,485 | A * | 11/1997 | Mock et al. | 239/102.2 |
| 6,536,682 | B1 * | 3/2003 | Schnupp et al. | 239/102.2 |
| 6,550,691 | B2 * | 4/2003 | Pence | 239/102.2 |

* cited by examiner

*Primary Examiner*—Kevin Shaver
*Assistant Examiner*—Darren Gorman
(74) *Attorney, Agent, or Firm*—Troxell Law Office, PLLC

(57) ABSTRACT

An aerosol impingement baffle, and more particularly, an aerosol impingement baffle employed in ultrasonic nebulizers, wherein the impingement orifices thereof are formed by disposing line-shaped impingement grooves at the inner breadth of the impingement baffle, thereby increasing the differentiation probabilities of liquid particles and avoiding congestions thereof.

3 Claims, 3 Drawing Sheets

AEROSOL IMPINGEMENT BAFFLE

BACKGROUND OF THE INVENTION (a) Field of the Invention

The invention relates to an aerosol impingement baffle, and more particularly, to an aerosol impingement baffle employed in ultrasonic nebulizers. The breadth of the impingement baffle is distributed with a plurality of line-shaped impingement grooves for reducing the probability of congestions thereof, thereby impinging liquids into aerosols in a well-spread manner.

(b) Description of the Related Art

Common ultrasonic applications concerning liquids, apart from cleaning by inducting ultrasonic waves into a liquid to clean the surface of an object through the sound wave oscillation thereof, such as ultrasonic cleanser for glasses, are also used in vaporizers, or medical equipment that impinge medical solutions into aerosols for skin steaming or providing inhalation therapy for the respiratory tract.

With respect to some aerosols produced for medication, in order to necessarily keep the operation thereof at low temperatures for avoiding physical and chemical reactions, ultrasonic is utilized to impinge a medical solution into an aerosol for inhalation by lungs or spraying over wounds; such equipment is extensively adopted. However, for ordinary ultrasonic nebulizers in medical equipment, orifices provided at the impingement baffles thereof are extremely small and thus often incur congestions.

SUMMARY OF THE INVENTION

An object of the invention is to provide an impingement baffle disposed with line-shaped impingement grooves so that congestions at the impingement baffle are not easily incurred, thereby offering a smooth formation of aerosol.

Another object of the invention is to arrange the line-shaped impingement grooves disposed at the impingement baffle in different directions according to the actions and operation requirements thereof.

Another object of the invention is to arrange the line-shaped impingement grooves disposed at the impingement baffle as any spiral waves or triangular waves.

The other object of the invention is to combine the impingement baffle and a piezoelectric ceramic by means of welding.

DESCRIPTION OF THE PREFERRED EMBODIMENTS

An aerosol impingement baffle in accordance with the invention, and more particularly, an aerosol impingement baffle employed in ultrasonic nebulizers, comprises an impingement baffle provided with line-shaped impingement grooves penetrated through the inner breadth thereof for avoiding congestions, thereby increasing directions for impinging liquids into particles for producing aerosols.

Figure 1:
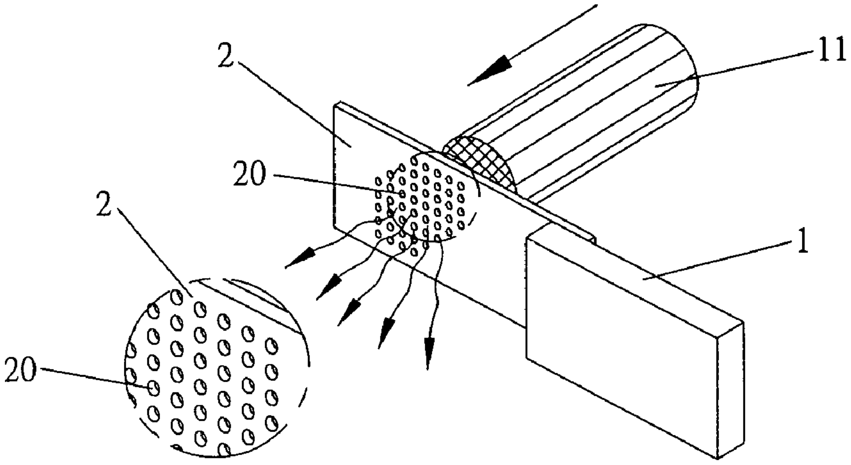
FIG. 1 Prior Art
FIG. 1 is a conventional schematic view showing the application of an impingement baffle in a prior ultrasonic nebulizer.

Referring to FIG. 1 showing a schematic view of an ultrasonic nebulizer in operation, wherein a piezoelectric ceramic 1 is adopted as an oscillator connected with an impingement baffle 2 at one side thereof, and oscillations of high frequencies are generated at the impingement baffle 2 from the actuation of the piezoelectric ceramic 1. The impingement baffle 2 is further provided with impingement orifices 20 at the inner breadth and a liquid supply 11 connected at the rear end thereof. The liquid supply 11 brings in a liquid through capillarity or water membranes, and through high-frequency oscillations of the impingement baffle 2, the liquid contained in the liquid supply 11 is impinged into particles forming an aerosol further forwarded to and discharged through the impingement orifices 20. In the present invention, unlike conventional combining methods, the piezoelectric ceramic 10 and the impingement baffle 200 are combined by welding using metals having high strengths. In conventional combining methods, chemical colloids having rigid texture and high transitivity are used. However, in conventional combining methods, particles thereof are prone to lose the binding force being crisp and become loose due to the rigid texture and thermal reactions. Therefore, in accordance with the invention, the piezoelectric ceramic 10 and the impingement baffle 200 are combined by welding using metals. The materials being welded are chosen based upon the degree of thermal resistance of the operating elements thereof without affecting the material operating characteristics as a principle.

Figure 2:
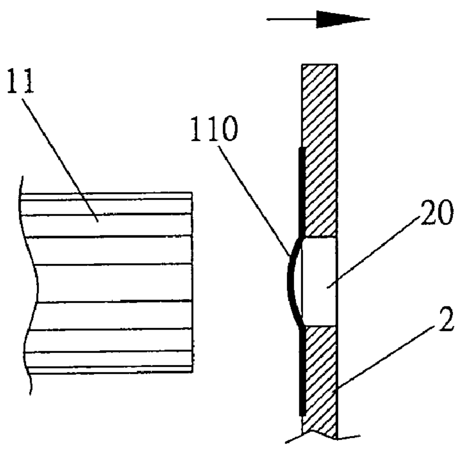
FIG. 2 Prior Art
FIG. 2 is a schematic view illustrating the first step of aerosol impingement.
Figure 3:
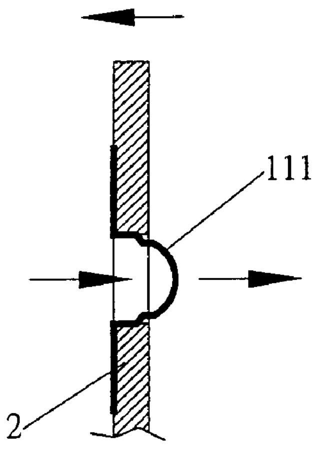
FIG. 3 Prior Art
FIG. 3 is a schematic view illustrating the second step of aerosol impingement.

Referring to FIGS. 2 and 3, the impingement orifices 20 provided at the impingement baffle 2 are oscillated back and forth relative to the liquid supply 11. During the process, the liquid is adhered relative to one side of the liquid supply 11 through the impingement orifices 20. The orifices 20 are extremely small openings having diameters between 1 to 15 microns, and thus the liquid thereof is adhered as water membranes 110. Through the reverse pulse of the oscillations thereof, an air pressure is produced for pushing a water membrane 110 and forming a water bubble 111 that explodes to the right side after receiving pressure. The water bubbles 111 are formed and exploded in progression according to the number of high-frequency oscillations, thus generating an explosive and pressurizing force as shown in FIG. 3. The force propels the indicated aerosol toward one side of the impingement baffle 2 and the aerosol is pressured and discharged such that the aerosol particles do not require additional itinerant impelling devices for achieving penetration effects as penetrated aerosols traveling upward in vaporizers.

Nevertheless, impingement orifices 20 provided in a prior impingement baffle 2 are openings of extremely small diameters and are consequently easily congested by dust or larger particles of medical solutions, and cleaning or replacement has to be performed for a rather limited number of usage. Furthermore, the impingement baffle 2 is a metal plate having a precision manufacturing not easily met and expensive production cost, and orifices thereof are liable to have different diameters that cannot be controlled within a certain standard range because the precision manufacturing thereof is an operation of high degree of difficulty. The diameters of the orifices are between 1 and 15 microns, and thus diameters of liquid droplets penetrated through the orifices having a 15-micron diameter are then comparatively larger to others. On top of that, owing to the physical property of liquid cohesion, liquid droplets are usually formed between the larger droplets of the aerosol, thus accumulating liquid around the aerosol outlet of the mechanism as in the prior nebulizers and failing to accomplish the fundamental aerosolization purpose. Also, aerosolized liquids generally contain impurities such as calcium that grow into adhesives through high-frequency oscillations, and white spots are then formed followed with congestion.

Therefore, the impingement orifices are improved in accordance with the invention for elevating the accuracy and efficiency of liquid aerosolization.

Figure 4:
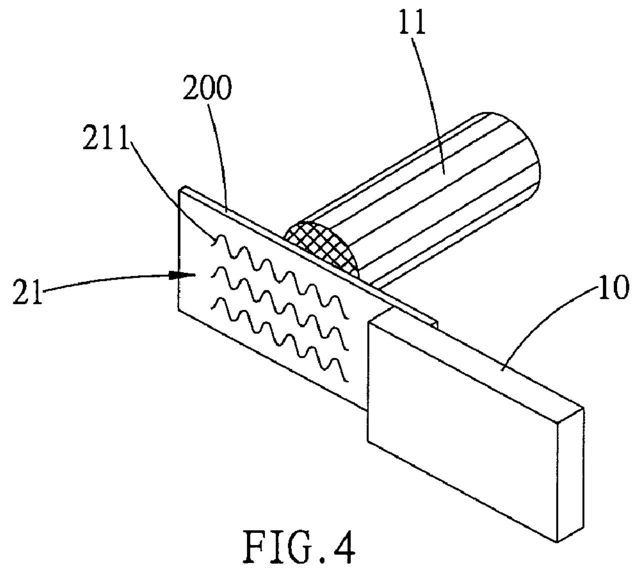
FIG. 4 is a first schematic view showing the distribution of the impingement baffle in accordance with the invention.
Figure 5:
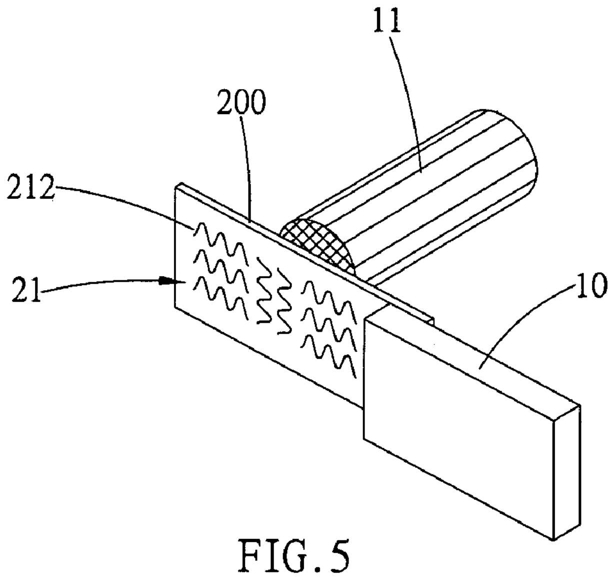
FIG. 5 is a second schematic view showing the distribution of the impingement baffle in accordance with the invention.

Referring to FIG. 4, a piezoelectric ceramic 10 is integrated with a impingement baffle 200 by means of suspended assembling, and one side of the impingement 200 is provided with a liquid supply 11 thereof. At an inner breadth of the impingement baffle 200 is disposed with line-shaped impingement grooves 21, and the grooves 21 are formed by S-shaped wave pattern grooves 211 that are 100 to 120 microns in width for favoring the processing thereof with low production cost as well as being not easily congested. Referring to FIG. 5, one side of the impingement baffle 200 is integrated with the piezoelectric ceramic and the other side of the impingement baffle 200 is provided with a liquid supply 11. The impingement grooves 21 disposed at the impingement baffle 200 may be arranged in horizontal or vertical distributions, or arranged to include both Horizontal-Vertical grooves 212 according to the material characteristics of the impingement baffle 200 or operating requirements. For instance, the middle part thereof is arranged in a vertical distribution for ensuring the mutual mechanical conjunction forces of the upper and lower sides of the impingement baffle 200.

Figure 6:
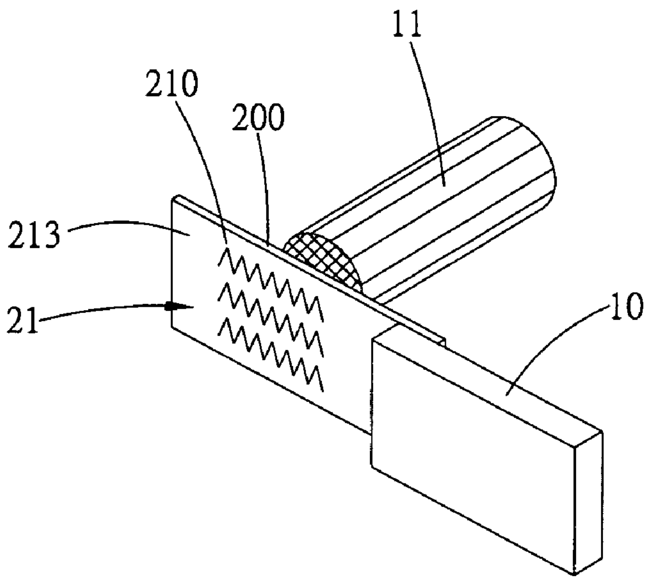
FIG. 6 is a third schematic view showing the distribution of the impingement baffle in accordance with the invention.

Referring to FIG. 6, one side of the impingement baffle 200 is integrated with the piezoelectric ceramic and the other side of the impingement baffle 200 is provided with a liquid supply 11. The impingement grooves 21 disposed at the impingement baffle 200 may be arranged as triangular waves grooves 213 to accumulate larger impingement energy at the peaks 210 for impinging the liquid thereof with high efficiency.

Figure 7:
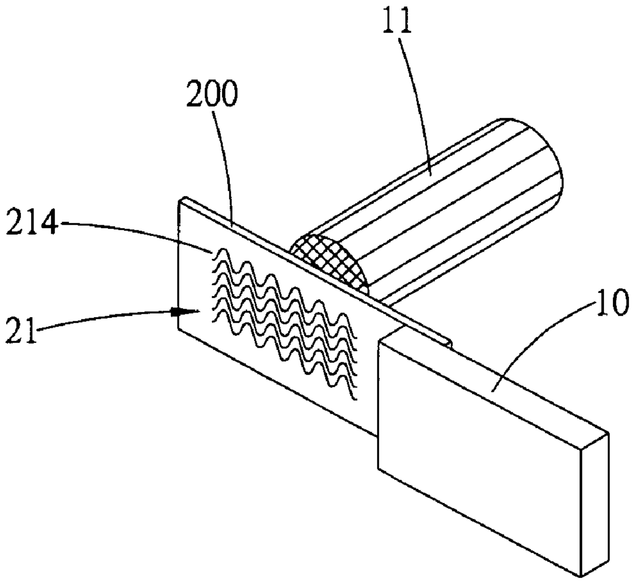
FIG. 7 is a fourth schematic view showing the distribution of the impingement baffle in accordance with the invention.

Referring to FIG. 7, one side of the impingement baffle 200 is integrated with the piezoelectric ceramic 10 and the other side of the impingement baffle 200 is provided with a liquid supply 11. The impingement grooves 21 disposed at the impingement baffle 200 may be arranged in an overlapping distribution to form numerous parallel array grooves 214 for increasing the number of impingement grooves 21 per unit area.

The above-mentioned embodiments disclose each kind of impingement grooves, such as grooves 211, 212, 213 and finally, grooves 214 disposed at the impingement baffle 200 are adhered to liquid membranes during oscillations to impinge the liquid thereof for forming aerosol particles as shown in FIGS. 2 and 3. The diameter of the orifices may be the same as that of the impingement grooves 21, and therefore the liquid particles may be adhered to the liquid membranes through liquid cohesion as shown in FIG. 2, and the liquid membranes are pressurized and exploded to have the aerosol discharged as shown in FIG. 3.

The provision of the grooves in accordance with the invention avoids congestions thereof, and the diameters of the aerosol particles impinged are also controlled within a certain range having a more simplified manufacturing processing and low production cost. In addition, the provision of the line-shaped grooves may be arranged in various distributions such as linear lines and angular lines for accommodating different requirements.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. An aerosol impingement baffle for an ultrasonic nebulizer comprising:

a) an impingement baffle having a plurality of impingement grooves, each of the plurality of impingement grooves being a wave shape; and b) a piezoelectric ceramic connected directly to the impingement baffle.

2. The aerosol impingement baffle according to claim 1, wherein each of the plurality of impingement grooves has a width in a range between 100 microns and 120 microns.

3. The aerosol impingement baffle according to claim 1, wherein the piezoelectric ceramic is connected directly to the impingement baffle by metal welding.

* * * * *